(12) United States Patent
Carreras

(10) Patent No.: US 11,241,371 B1
(45) Date of Patent: Feb. 8, 2022

(54) SKIN PROTECTANT

(71) Applicant: Janis Isabel Carreras, Warrenton, VA (US)

(72) Inventor: Janis Isabel Carreras, Warrenton, VA (US)

(*) Notice: Subject to any disclaimer, the term of this patent is extended or adjusted under 35 U.S.C. 154(b) by 94 days.

(21) Appl. No.: 16/793,181

(22) Filed: Feb. 18, 2020

(51) Int. Cl.
*A61K 8/29* (2006.01)
*A61K 8/27* (2006.01)
*A61K 8/89* (2006.01)
*A61K 8/41* (2006.01)
*A61K 8/42* (2006.01)
*A61K 8/49* (2006.01)
*A61K 8/81* (2006.01)
*A61K 8/31* (2006.01)
*A61Q 17/04* (2006.01)

(52) U.S. Cl.
CPC ............. *A61K 8/29* (2013.01); *A61K 8/27* (2013.01); *A61K 8/31* (2013.01); *A61K 8/416* (2013.01); *A61K 8/42* (2013.01); *A61K 8/4973* (2013.01); *A61K 8/8147* (2013.01); *A61K 8/89* (2013.01); *A61Q 17/04* (2013.01)

(58) Field of Classification Search
None
See application file for complete search history.

(56) References Cited

U.S. PATENT DOCUMENTS

| | | | | |
|---|---|---|---|---|
| 5,620,631 A | * | 4/1997 | Heiskel | A61K 8/046 424/45 |
| 7,135,165 B2 | | 11/2006 | Zofchak et al. | |
| 8,529,877 B2 | * | 9/2013 | Wagner | A61K 8/55 424/70.1 |
| 10,124,030 B2 | | 11/2018 | Goldsberry et al. | |
| 2018/0193236 A1 | * | 7/2018 | Son | A61K 8/898 |
| 2018/0303448 A1 | * | 10/2018 | SaNogueira | A61K 8/891 |

OTHER PUBLICATIONS

Ashland (Ashland, Hair Care, Ingredients Portfolio, (2017) Covington, KY). (Year: 2017).*

* cited by examiner

*Primary Examiner* — Dominic Lazaro
(74) *Attorney, Agent, or Firm* — Sanchelima & Associates, P.A.; Christian Sanchelima; Jesus Sanchelima

(57) ABSTRACT

A skin protecting product that includes cyclopentasiloxane, disiloxane, octylacrylamide, acrylates, butylaminoethyl methacrylate copolymer, isopropyl myristate, hydroxypropyl gluconomide, hydroxyproply ammonium gluconate, phenoxyethanol, Cetearyl alcohol, cetyl alcohol, cetyl PPG, PPG-10/1 dimethicone, hydroxyethyl urea, zinc oxide, titanium oxide, fragrance such as perfumes or colognes, vitamin C, and isodecyl neopentanoate. The skin protecting product is applied daily along with sunscreen to help reduce the chance of skin damage related conditions and illnesses that result from sun exposure. The product is applied on hard to reach areas such as the scalp. The product is weightless, so the user is not bothered by the application of the product. The skin protecting product comes in various forms such as a spray, gel or lotion.

11 Claims, No Drawings

SKIN PROTECTANT

BACKGROUND OF THE INVENTION

1. Field of the Invention

The present invention relates to a skin protectant and, more particularly, to a skin protectant that is intended to be used daily along with other skin products such as sunscreen to help reduce the chance of skin related illnesses and cancers.

2. Description of the Related Art

Several designs for skin protectants have been designed in the past. None of them, however, include a combination skin care lotion and sun screen including cyclopentasiloxane, disiloxane, octylacrylamide, acrylates, butylaminoethyl methacrylate copolymer, isopropyl myristate, hydroxypropyl gluconomide, hydroxyproply ammonium gluconate, phenoxyethanol, Cetearyl alcohol, cetyl alcohol, cetyl PPG, PPG-10/1 dimethicone, hydroxyethyl urea, zinc oxide, titanium oxide, fragrance, including perfume or colognes, vitamin C, and isodecyl neopentanoate. The skin protectant product is intended to be used daily to help prevent pre cancers, cancers and other harmful skin conditions. The skin protectant product comes in a variety of forms such as a mist spray, a lotion, a gel or other suitable compositions and forms. The skin protectant product may be helpful to allow application of skin protection in hard to reach areas as well.

Applicant believes that a related reference corresponds to U.S. Pat. No. 10,124,030 for a topical skin care solution comprising at least zinc oxide, cetearyl alcohol, and phenoxyethanol for moisturizing the skin and protecting the skin from sun damage. Applicant believes another related reference corresponds with U.S. Pat. No. 7,135,165 for a combined skin moisturizing lotion and sunscreen. None of these references, however, teach of a skin protecting product that includes the aforementioned ingredients to provide a skin protectant that can be used daily in combination with a sunscreen to help reduce sun damage and related conditions.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a skin protectant that includes a combination of ingredients lacking in the prior art.

It is another object of this invention to provide a skin protectant that acts as a barrier to protect a user from harmful sunrays.

It is still another object of the present invention to provide a skin protectant that helps to reduce the chance of harmful skin conditions and illnesses such as skin cancer from sun exposure.

It is another object of the present invention to provide a skin protectant that can be applied on hard to reach areas such as the scalp and ears which are typically difficult to apply anything to.

It is yet another object of the present invention to provide a skin protectant that is lightweight to keep the hair and skin feeling soft and greaseless.

It is still another object of the present invention to provide a skin protectant that comes a in a variety of forms such as a spray, a mist, a gel, a lotion or other similar suitable forms.

It is yet another object of this invention to provide such a skin protectant that is inexpensive to implement and maintain while retaining its effectiveness.

Further objects of the invention will be brought out in the following part of the specification, wherein detailed description is for the purpose of fully disclosing the invention without placing limitations thereon.

DETAILED DESCRIPTION OF THE EMBODIMENTS OF THE INVENTION

The present invention is generally referred to with numeral 10, it can be observed that it, a skin protectant 10, basically includes numerous ingredients that help to provide protection from the sun to help reduce the chances of harmful and dangerous skin conditions such as cancer. The composition of the skin protectant can be included in a variety of different skin protecting products.

Skin protectant 10 may be applied daily along with sunscreen in order to provide the most protection possible. It may be suitable to apply the present invention to prevent harmful skin conditions that may be costly or painful to treat and even deadly in some cases if left untreated. Skin protectant 10 provides preventive means. Some of those conditions that may be prevented may be pre cancer conditions or cancerous conditions. It should be understood that, preferably, the present invention, is not a substitute for sunscreen, but rather a supplement. Skin protectant 10 may preferably be applied to the scalp, hair, ears and neck. These are typically neglected areas when it comes to applying adequate skin protection thereto. However, it should be understood that the present invention may be suitable to apply elsewhere on the body. The present invention serves as a barrier between the skin of a user and the harmful sunrays. The present invention is beneficial in that it may be weightless and greaseless as to feel as if it is not even being worn by the user. Hair and skin covered by the present invention should still be soft and residue free. The skin protecting product may advantageously come in different forms such as a spray, a mist, a gel, a dry spray, a lotion or other similar suitable forms as necessary. The present invention may also be suitable to use by users of all ages without health concerns resulting.

It should be understood that there may be variations to the ingredients of the present invention depending on the medium used to dispense the present invention and further depending on the consistency of the product.

Generally, the core ingredients, for the present invention include: cyclopentasiloxane, disiloxane, octylacrylamide, acrylates, butylaminoethyl methacrylate copolymer, isopropyl myristate, hydroxypropyl gluconomide, hydroxyproply ammonium gluconate, phenoxyethanol, Cetearyl alcohol, cetyl alcohol, cetyl PPG, PPG-10/1 dimethicone, hydroxyethyl urea, zinc oxide, titanium oxide, fragrance or perfume or colognes, vitamin C, and isodecyl neopentanoate.

It may be suitable for the present invention to also include butane, isobutane or propane, which are compressed gasses, that may be used as aerosol propellants in certain embodiments of the present invention. It may also be suitable for the present invention to include a combination of butane, isobutane and propane. The present invention may also include water as an ingredient primarily as a solvent to dissolve and also possibly to form emulsion in which the water and oils combine to form creams or lotions.

The following are ingredients as mentioned above and their benefits and roles in the present invention.

Cyclopentasiloxane may be mainly used as a conditioner, delivery agent, lubricant and solvent. This ingredient helps to provide a silky and soft feeling without creating a heavy weighted down feeling and greasy residue, especially on hair.

Disiloxane, which preferably evaporates, may help to provide a silky and soft feeling to the area on which the present invention is applied to. Disiloxane further allows for great spreadability of the present invention once it is being applied to the body.

Octylacrylamide may help as a film forming and fixative agent that may produce a smooth and glossy finish when applied to the hair or skin of the user. This finish may be preferable over the white and greasy residue that may result otherwise.

Acrylates may be included to function as a stabilizer that helps to set hair, add volume and body to the hair and further protect the hair from humidity, should the present invention be applied to the scalp and hair of the user. The hair and scalp area are difficult to apply product to and that results in seldomly any protection being provided thereto. However, this helps facilitates the application of the present invention to such areas.

The present invention may further include butylaminoethyl methacrylate copolymer to function as a film forming element. Butylaminoethyl methacrylate copolymer may further help as an antistatic and hair fixing ingredient.

Isopropyl myristate may be used as a synthetic oil that can be used as an emollient, thickening agent and lubricant within the present invention. This may help the present invention to form properly depending on the form that it takes.

The present invention may also include hydroxypropyl gluconomide and hydroxyproply ammonium gluconate which may help to strength and repair the hair of the user. It may be preferable that hydroxypropyl gluconomide and hydroxyproply ammonium gluconate be used together.

Phenoxyethanol may be used as a preservative, stabilizer and fragrance ingredient that may help to limit bacterial growth.

Cetearyl alcohol and cetyl alcohol are primarily fatty alcohols within the present invention. Cetearyl alcohol and cetyl alcohol are emollients that may help to soften the hair and skin of the user when the present invention is applied.

Cetyl PPG and PPG-10/1 dimethicone may function as a skin conditioning agent. Cetyl PPG and PPG-10/1 dimethicone may be a synthetic chemical that includes dimethicone. This helps to have the skin prepped and ready for the other ingredients to be received and absorbed properly. It may be preferable that Cetyl PPG and PPG-10/1 dimethicone be used together.

Hydroxyethyl urea may be a moisturizing agent. Preferably, hydroxyethyl urea may be colorless and odorless. It may be suitable for hydroxyethyl urea to be a solution that is at least half aqueous. Hydroxyethyl urea may hydrate the skin of the user. Hydroxyethyl urea may also aid in maintaining a normal moisture balance in the skin and more specifically, in the skin's uppermost layer.

The present invention may use zinc oxide and titanium dioxide as an active ingredient. Zinc oxide may be more effective than titanium dioxide. Titanium dioxide may be effective at blocking ultraviolet B and short-wave ultraviolet A rays. However, long ultraviolet rays are blocked better by zinc oxide. Zinc oxide and titanium dioxide may be used in combination as well within the present invention.

The present invention may be scented and may include a fragrance. However, it may also be suitable for the present invention to be odorless. The scents may be suitable for men or women as necessary. The fragrance may come in the form of perfume oils dissolved in water and alcohol. The fragrance may also come in the form of cologne oils or oils diluted with water and alcohol. Fragrance may be suitable in the form of a cologne, a perfume or combinations thereof.

The present invention may further include vitamin C. Vitamin C may be used to absorb iron. Iron may be necessary to absorb as it helps to maintain hair strong and healthy. Additionally, hair thinning may be prevented with vitamin C and the absorption of iron.

Isodecyl neopentanoate, which be allow for the hair and skin to be softened and sooth the skin of the user. Further, isodecyl neopentanoate may serve as a protective layer.

The composition can be effectively implemented in the following ranges by percent by weight in the present invention comprising:

a. approximately 0.1-0.3% Cyclopentasiloxane by weight;
b. approximately 0-19% Disiloxane by weight;
c. approximately 0.5-3% Octylacrylamide by weight;
d. approximately 1-15% Acrylates by weight;
e. approximately 0.5-1% Butylaminoethyl Methacrylate Copolymer by weight;
f. approximately 0.5-2.5% Isopropyl Myristate by weight;
g. approximately 0-0.2% Hydroxypropyl Gluconamide by weight;
h. approximately 0-0.2% Hydroxypropyl Ammonium Gluconate by weight;
i. approximately 0-0.5% Phenoxyethanol by weight;
j. approximately 0.5-10% Cetearyl alcohol by weight;
k. approximately 0.5-10% Cetyl alcohol by weight;
l. approximately 0-0.5% Cetyl PPG by weight;
m. approximately 0-0.5% PPG-10/1 Dimethicone by weight;
n. approximately 0-0.2% Hydroxyethyl Urea by weight;
o. approximately 0-0.5% Fragrance by weight;
p. approximately 0-0.6% Vitamin C by weight;
q. approximately 0.5-1.2% Isodecyl Neopentanoate by weight;
r. approximately 15-20% Zinc Oxide by weight; and
s. approximately 0-7.5% Titanium Oxide by weight.

Optionally, the composition may further include these other ingredients:

a. approximately 30-90% Butane by weight;
b. approximately 30-90% Isobutane by weight; and
c. approximately 30-90% Propane by weight.

It should be understood that the present invention may allow a user to protect their skin, hair and scalp from sun exposure which can lead to skin conditions such as pre cancer and cancer. The present invention may come in various forms that may different in ingredients slight to allow for the dispensing through the desired medium properly. Preferably, the present invention may be used with sunscreen to protect by serving as a barrier.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A composition for a skin protectant, consisting essentially of:
   a. cyclopentasiloxane;
   b. disiloxane;
   c. octylacrylamide;
   d. acrylates;
   e. butylaminoethyl methacrylate copolymer;
   f. isopropyl myristate;
   g. hydroxypropyl gluconamide;
   h. hydroxypropyl ammonium gluconate;
   i. phenoxyethanol;
   j. cetearyl alcohol;
   k. cetyl alcohol;
   l. cetyl polypropylene glycol (cetyl PPG);
   m. polypropylene glycol-10/1 dimethicone (PPG-10/1 dimethicone);
   n. hydroxyethyl urea;
   o. fragrance;
   p. vitamin C;
   q. isodecyl neopentanoate;
   r. zinc oxide; and
   s. titanium oxide.

2. The composition set forth in claim 1 consisting of butane.

3. The composition set forth in claim 2, further consisting of butane between 30% and 90% of the total weight.

4. The composition set forth in claim 1 further consisting of isobutane.

5. The composition set forth in claim 4, further consisting of isobutane between 30 and 90% of the total weight of said.

6. The composition set forth in claim 1 further consisting of propane.

7. The composition set forth in claim 1 further consisting of propane between 30 and 90% of the total weight.

8. The composition set forth in claim 1 consisting essentially of:
   a. between 0.1 and 0.3% of said cyclopentasiloxane by weight;
   b. up to 19% of said disiloxane by weight;
   c. between 0.5 and 3% of said octylacrylamide by weight;
   d. between 1 and 15% of said acrylates by weight;
   e. between 0.5 and 1% of said butylaminoethyl methacrylate copolymer by weight;
   f. between 0.5 and 2.5% of said isopropyl myristate by weight;
   g. up to 0.2% of said hydroxypropyl gluconamide by weight;
   h. up to 0.2% of said hydroxypropyl ammonium gluconate by weight;
   i. up to 0.5% of said phenoxyethanol by weight;
   j. between 0.5 and 10% of said cetearyl alcohol by weight;
   k. between 0.5 and 10% of said cetyl alcohol by weight;
   l. up to 0.5% of said cetyl polypropylene glycol (cetyl PPG) by weight;
   m. up to 0.5% of said polypropylene glycol-10/1 dimethicone (PPG-10/1 dimethicone) by weight;
   n. up to 0.2% of said hydroxyethyl urea by weight;
   o. up to 0.5% of said fragrance by weight;
   p. up to 0.6% of said vitamin C by weight;
   q. between 0.5 and 1.2% of said isodecyl neopentanoate by weight;
   r. between 1 and 20% of said zinc oxide by weight; and
   s. up to 7.5% of said titanium oxide by weight.

9. The composition set forth in claim 1 further consisting of water.

10. A composition for a skin protectant, consisting essentially of:
    a. butane;
    b. isobutane;
    c. propane;
    d. cyclopentasiloxane;
    e. disiloxane;
    f. octylacrylamide;
    g. acrylates;
    h. butylaminoethyl methacrylate copolymer;
    i. isopropyl myristate;
    j. hydroxypropyl gluconamide;
    k. hydroxypropyl ammonium gluconate;
    l. phenoxyethanol;
    m. cetearyl alcohol;
    n. cetyl alcohol;
    o. cetyl polypropylene glycol (cetyl PPG);
    p. polypropylene glycol-10/1 dimethicone (PPG-10/1 dimethicone);
    q. hydroxyethyl urea;
    r. fragrance;
    s. vitamin C;
    t. isodecyl neopentanoate;
    u. zinc oxide; and
    v. titanium oxide.

11. The composition set forth in claim 1 consisting essentially of:
    a. between 30 and 90% of said butane by weight;
    b. between 30 and 90% of said isobutane by weight;
    c. between 30 and 90% of said propane by weight;
    d. between 0.1 and 0.3% of said cyclopentasiloxane by weight;
    e. up to 19% of said disiloxane by weight;
    f. between 0.5 and 3% of said octylacrylamide by weight;
    g. between 1 and 15% of said acrylates by weight;
    h. between 0.5 and 1% of said butylaminoethyl methacrylate copolymer by weight;
    i. between 0.5 and 2.5% of said isopropyl myristate by weight;
    j. up to 0.2% of said hydroxypropyl gluconamide by weight;
    k. up to 0.2% of said hydroxypropyl ammonium gluconate by weight;
    l. up to 0.5% of said phenoxyethanol by weight;
    m. up to 0.5% of said cetearyl alcohol alcohol by weight;
    n. between 0.5 and 10% of said cetyl alcohol by weight;
    o. up to 0.5% of said cetyl polypropylene glycol (cetyl PPG) by weight;
    p. up to 0.5% of said polypropylene glycol-10/1 dimethicone (PPG-10/1 dimethicone) by weight;
    q. up to 0.2% of said hydroxyethyl urea by weight;
    r. up to 0.5% of said fragrance by weight;
    s. up to 0.6% of said vitamin C by weight;
    t. between 0.5 and 1.2% of said isodecyl neopentanoate by weight;
    u. between 1 and 20% of said zinc oxide by weight; and
    v. up to 7.5% of said titanium oxide by weight.

* * * * *